United States Patent
Petersen et al.

(10) Patent No.: US 7,850,905 B2
(45) Date of Patent: Dec. 14, 2010

(54) ON BOARD MONITOR FOR ENDOSCOPE REPROCESSOR

(75) Inventors: Michael P. Petersen, Eden Prairie, MN (US); Paul T. Feld, Buffalo, MN (US)

(73) Assignee: Minntech Corporation, Minneapolis, MN (US)

( * ) Notice: Subject to any disclaimer, the term of this patent is extended or adjusted under 35 U.S.C. 154(b) by 1206 days.

(21) Appl. No.: 11/068,575

(22) Filed: Feb. 28, 2005

(65) Prior Publication Data

US 2005/0196314 A1  Sep. 8, 2005

Related U.S. Application Data

(60) Provisional application No. 60/550,129, filed on Mar. 4, 2004.

(51) Int. Cl.
*A61L 2/00* (2006.01)
*A61L 2/08* (2006.01)

(52) U.S. Cl. .................. 422/2; 422/27; 422/28
(58) Field of Classification Search ................ 600/133; 422/2–3, 25–26, 106, 108–113
See application file for complete search history.

(56) References Cited

U.S. PATENT DOCUMENTS

| | | | |
|---|---|---|---|
| 4,862,872 A | 9/1989 | Yabe et al. | |
| 5,494,530 A | 2/1996 | Graf | |
| 5,858,305 A * | 1/1999 | Malchesky | 422/28 |
| 5,882,589 A | 3/1999 | Mariotti | |
| 5,882,590 A * | 3/1999 | Stewart et al. | 422/28 |
| 6,148,415 A * | 11/2000 | Kobayashi et al. | 714/15 |
| 6,260,560 B1 | 7/2001 | Walta | |
| 6,452,624 B1 * | 9/2002 | Aloy | 348/71 |
| 6,641,781 B2 | 11/2003 | Walta | |
| 6,984,359 B2 * | 1/2006 | Florkey et al. | 422/3 |
| 2002/0001537 A1 | 1/2002 | Hlebovy et al. | |
| 2006/0251540 A1 * | 11/2006 | Benning et al. | 422/3 |

FOREIGN PATENT DOCUMENTS

EP   0 709 056 A1   5/1996

\* cited by examiner

*Primary Examiner*—Philip R Smith
(74) *Attorney, Agent, or Firm*—Faegre & Benson LLP

(57) ABSTRACT

An on board monitor for an endoscope reprocessor for monitoring the performance and order of a predetermined set of critical steps for reprocessing an endoscope. The monitor will only allow the overall system to reach the last step indicating successful completion of the process related to the critical steps representing successful reprocessing of an endoscope after the system successfully completes all of the previous critical steps and in the correct order.

21 Claims, 11 Drawing Sheets

Fig. 10

| T | Temperature is within predetermined limits |
|---|---|
| L | Input is LOW |
| H | Input is HIGH |
| P | Output is POWERED |
| R | Output is RELEASED |
| 1 | Volume is ≤ predetermined low level |
| 2 | Volume is ≤ predetermined medium level |
| 3 | Volume is ≥ predetermined high level |

ON BOARD MONITOR FOR ENDOSCOPE REPROCESSOR

CROSS REFERENCE TO RELATED APPLICATION

This application claims the benefit of U.S. Provisional Application No. 60/550,129 filed Mar. 4, 2004, the entire contents of which are hereby expressly incorporated by reference.

BACKGROUND OF THE INVENTION

Many of the medical products today are controlled by software. The process of documenting, testing, verifying, and updating the software is becoming more mature. The methods that are used to assure proper operation of the software, and therefore the proper operation of the medical product are time consuming. As the software becomes more and more complex, the required testing and documentation grows dramatically. The off-the-shelf software and operating systems (such as the operating system available from Microsoft under the trademark Windows) have grown in complexity and flexibility. It is possible to interface with data bases, LAN systems, WAN systems, Internet, application programs, and literally tens of thousands of third party software packages. This flexibility is a great advantage to medical products but the complexity of the software, and the inability of the manufacturer to know what other software products might be added at a later date, make complete testing of the software virtually impossible.

For this reason, most medical products do not use standard operating systems such as the Windows operating system. They incorporate their own operating systems or put huge restrictions on the operating system they do use to limit the complexity and changeability, and therefore the flexibility of the system. These restrictions are imposed to assure the proper operation of the medical product. One example of this problem is seen with a prior art endoscope reprocessing system controlled by a standard computer, typically a PC (personal computer). This allows the flexibility to use standard data base programs to track the endoscopes and their reprocessing history. Modem computer and communications technology provide the ability to network systems together and interface directly with hospital computer systems. The capability exists to incorporate off-the-shelf bar code readers for tracking products (to reduce human error) and use endoscope identification features so the endoscope type is automatically transmitted to both the reprocessing machine and to one or more computers which store data about the endoscopes and their reprocessing. One problem with using a standard computer is the inability to completely test the software code to assure that no software bugs or errors exist in that code. Even if one were to spend the time it would take to test the code in every conceivable condition, the testing would need to be repeated as soon as new software (even an upgrade) was installed on the system.

With the proliferation of software viruses, this problem becomes even more critical. It would be possible to have perfect code when the system was installed only to have a virus get into the code and change it to a condition that would cause improper operation of the medical product.

One possible solution to this problem is to have a second computer monitoring the first computer to assure that everything it is doing is correct. This complicates the situation as it is then necessary to program and test a second system, and take steps to prevent the second system from also being exposed to a virus.

The present invention solves this problem by having a separate monitor system between the main operating computer and the actual hardware of the medical product, in this case the endoscope reprocessor. This monitor system can be as simple as a PLC (programmable logic controller) with some intelligence or as complicated as a second microprocessor operating on imbedded software (i.e. non-Windows operating system software or equivalent). The main function of the monitor system software is to monitor the critical steps or parameters of the medical reprocessor product (or other medical product, it being understood that the present invention is not limited to reprocessing endoscopes, but is suitable for and encompasses processing other medical products requiring satisfactory performance of a series of critical steps in the processing or reprocessing of the medical device). For instance (in the endoscope reprocessor example) the monitoring system would insure that the correct steps were performed to disinfect, clean and rinse the endoscope.

By "cleaning" is meant the removal of physical debris from the endoscope. By "disinfecting" is meant the inactivation of biologically active material from the endoscope to a predetermined degree. An example of disinfection is the killing, inhibition, or removal of microorganisms that cause disease. Disinfection may not necessarily eliminate spores or all of the microorganisms from an object or environment. By "sterilizing" is meant the inactivation of biologically active material to a predetermined degree greater than disinfecting. An example of sterilization is a process in which all living cells, spores and viruses are completely destroyed or removed from an object or environment. It is to be understood that while the present invention is described herein with respect to disinfecting and disinfection, the present invention may be used to perform a process that includes only cleaning, or cleaning and disinfecting or disinfecting without cleaning. Furthermore, the present invention may also be used with a process that performs or includes sterilizing, either alone or in combination with cleaning.

In the practice of the present invention, the monitor system has the ability to take control of the hardware performing the processing or reprocessing. In particular with respect to the endoscope reprocessing example, the monitor system will keep the lid (or other access) of the reprocessor closed and not allow it to open (or provide access) until the endoscope is properly reprocessed, or (in the event of an error, access will be denied until the computer acknowledges the error and alerts the operator). It is to be understood that "lid" refers to a means of controlling access to the medical device being processed or reprocessed according to the present invention. If the computer code gets lost or causes improper critical commands (or an improper sequence of commands) to be sent to the reprocessor hardware, the monitor system will provide a warning to the operator that the endoscope has not been properly reprocessed. The monitor system has the ability to communicate directly with the operator. One or more human perceptible indicators, such as visual indicator lights or audible indicator annunciators may be used in the practice of the present invention to indicate normal and or abnormal operating conditions or status of the reprocessing, or that the monitor system has detected a problem.

This arrangement allows the PC or other computer to use its flexibility to the maximum. It can be connected to networks, the web, and any extra software that is needed. The monitor will assure that the medical device works properly. With this arrangement, the monitor system code can go through extensive testing and validation in a reasonable time as it is self-contained and controlled by the manufacturer. The integrity of the medical device and its operation is able to be controlled by well-tested software and the flexibility and upgradability of the computer is not lost.

As mentioned above, while it is possible to use a redundant computer to monitor the operation of the first system, such redundant computer systems often become as complicated as the original system, require extensive testing and are therefore impractical for an application such as endoscope reprocessing.

In contrast, the present invention allows complete software validation of that software that controls the critical aspects of a system without requiring complete validation of a general operating system or applications programs that may be present and active.

The aspects of the invention which are believed to be different from and preferred over known products, machines, processes, or business methods are, in particular, the separation of the critical steps to assure the fact of execution of each critical step and the proper performance of each such step by monitoring with a system that has the ability to directly control the hardware in the event it observes an improper condition.

The present invention has applicability to medical products beyond endoscopes. It could be used for any software controlled system that controls critical steps or processes in relation to a medical device.

BRIEF DESCRIPTION OF THE DRAWINGS

FIG. 10 is a table showing an example of critical steps along with respective inputs and outputs to illustrate certain aspects of the present invention.

FIG. 11 is a table showing a key for abbreviations used in FIG. 10.

DETAILED DESCRIPTION

One example of a system for cleaning, disinfecting and/or drying endoscopes is shown in U.S. Pat. No. 6,641,781 B2, issued Nov. 4, 2003, and the entire contents thereof are hereby incorporated by reference.

Another example of a device and method for cleaning and/or disinfecting endoscopes is shown in U.S. Pat. No. 6,260,560 B1, issued Jul. 17, 2001, and the entire contents thereof are hereby incorporated by reference.

Still another example of a device and method for cleaning and/or disinfecting endoscopes is shown in European Patent Application EP 0 709 056 A1, published Jan. 5, 1996, and the entire contents thereof are hereby incorporated by reference.

Figure 1:
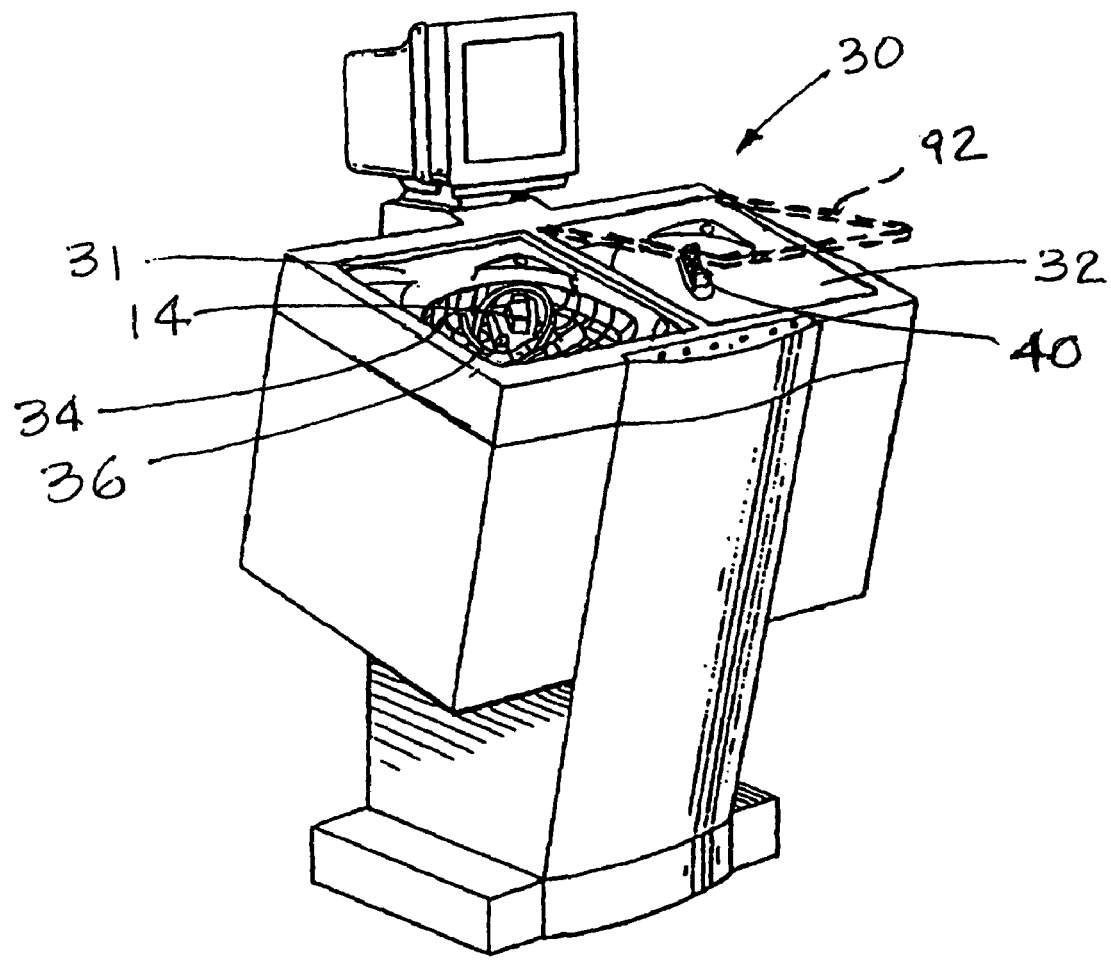
FIG. 1 is a very diagrammatic view in perspective of a prior art apparatus of the type useful for reprocessing endoscopes.

Referring now most particularly to FIG. 1, a disinfecting device or endoscope reprocessor 30 may be seen. The disinfecting device 30 is provided with two trays 31 and 32 in which a rack 34 is, with an endoscope 36 therein, can be accommodated. In FIG. 1, a rack of this nature is located in the left hand tray. Both trays 31 and 32 are provided with a counter-connection block which, when a rack 34 is placed in the tray 31, 32, can be connected to the connection block 38 arranged in rack 34. The counter-connection block arranged in the right hand tray can be seen in FIG. 1 and is denoted by the reference numeral 40.

Figure 2:
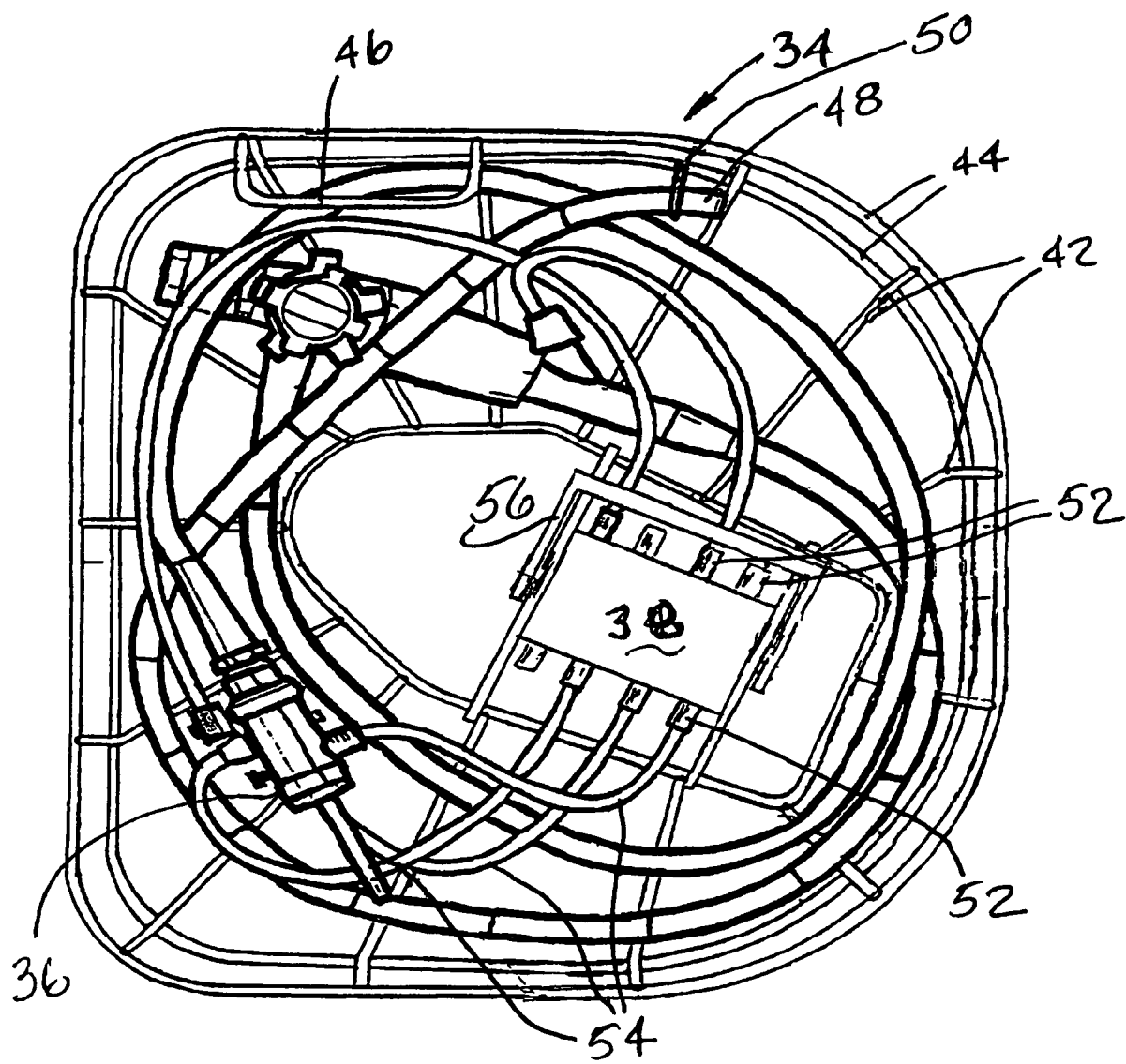
FIG. 2 is a plan view of a prior art rack with an endoscope therein suitable for use with the apparatus of FIG. 1.

Referring now also to FIG. 2, the rack 34 may be formed from bent rods 42 and 44 which are fixedly connected to one another. The rack 34 is provided with one or two handles 46, by means of which the rack can be gripped and lifted up. The rack 34 is furthermore formed in such a manner that an endoscope 36 can be placed therein in a more or less folded state. In order to be able to fix in particular the fragile end 48 of the endoscope, the rack may be provided with a tip holder 50.

The connection block 38 is arranged fixedly in the rack. This connection block is provided with passages and ports 52 which are connected to the passages and can be connected to the passages of the endoscope 36 by means of flexible tubes 54. On its underside (not visible in FIG. 2), the connection block 38 is provided with connection points for the connection of counter-connection blocks in either basin 31 or 32 of device 30. The connection block 38 is furthermore provided with a handle 56. By moving the handle 56, the connection block 38 can be connected to a counter-connection block or removed therefrom.

Figure 3:
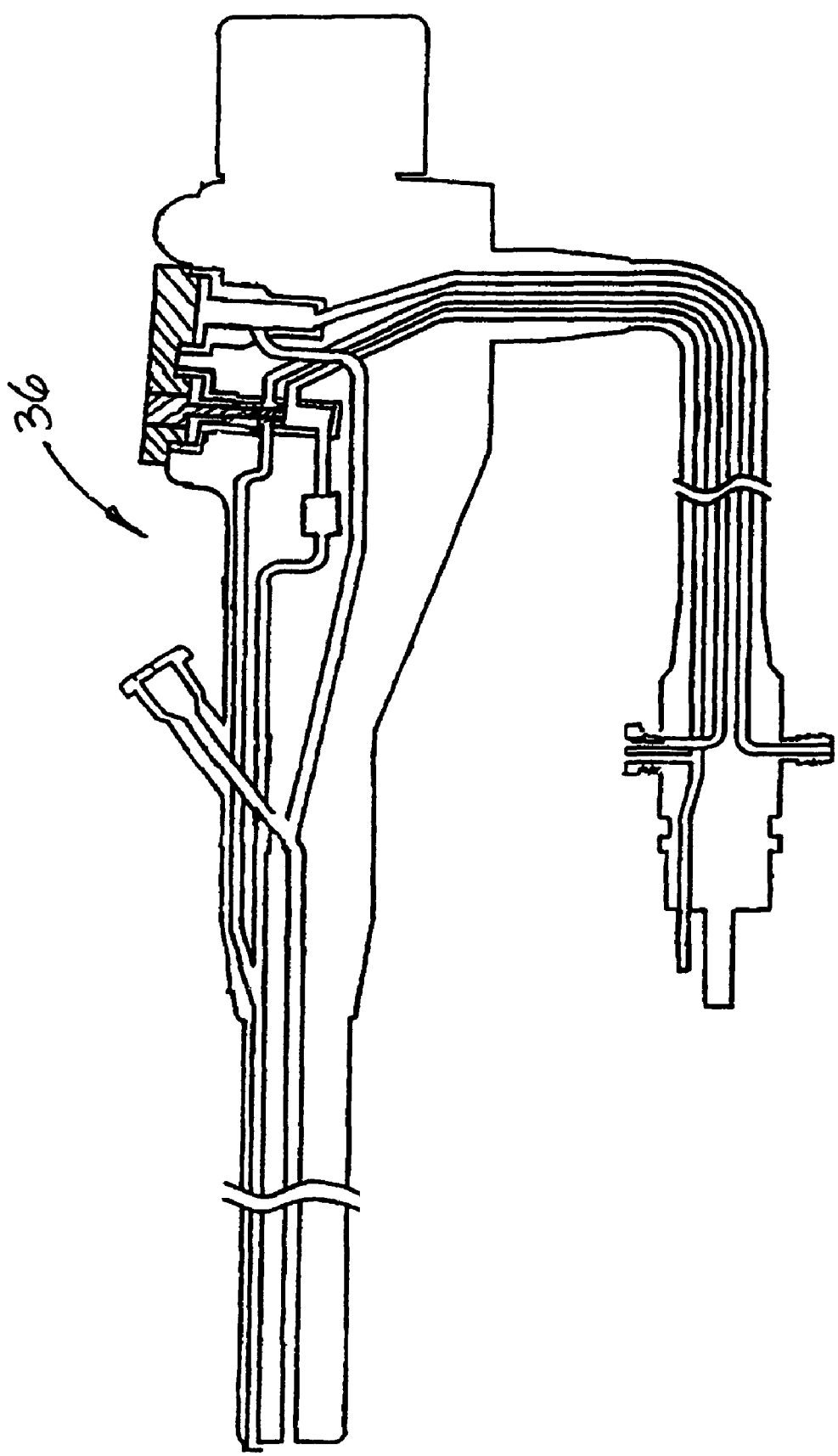
FIG. 3 is simplified diagrammatic view of a certain prior art type of endoscope suitable for reprocessing in the practice of the present invention.
Figure 4:
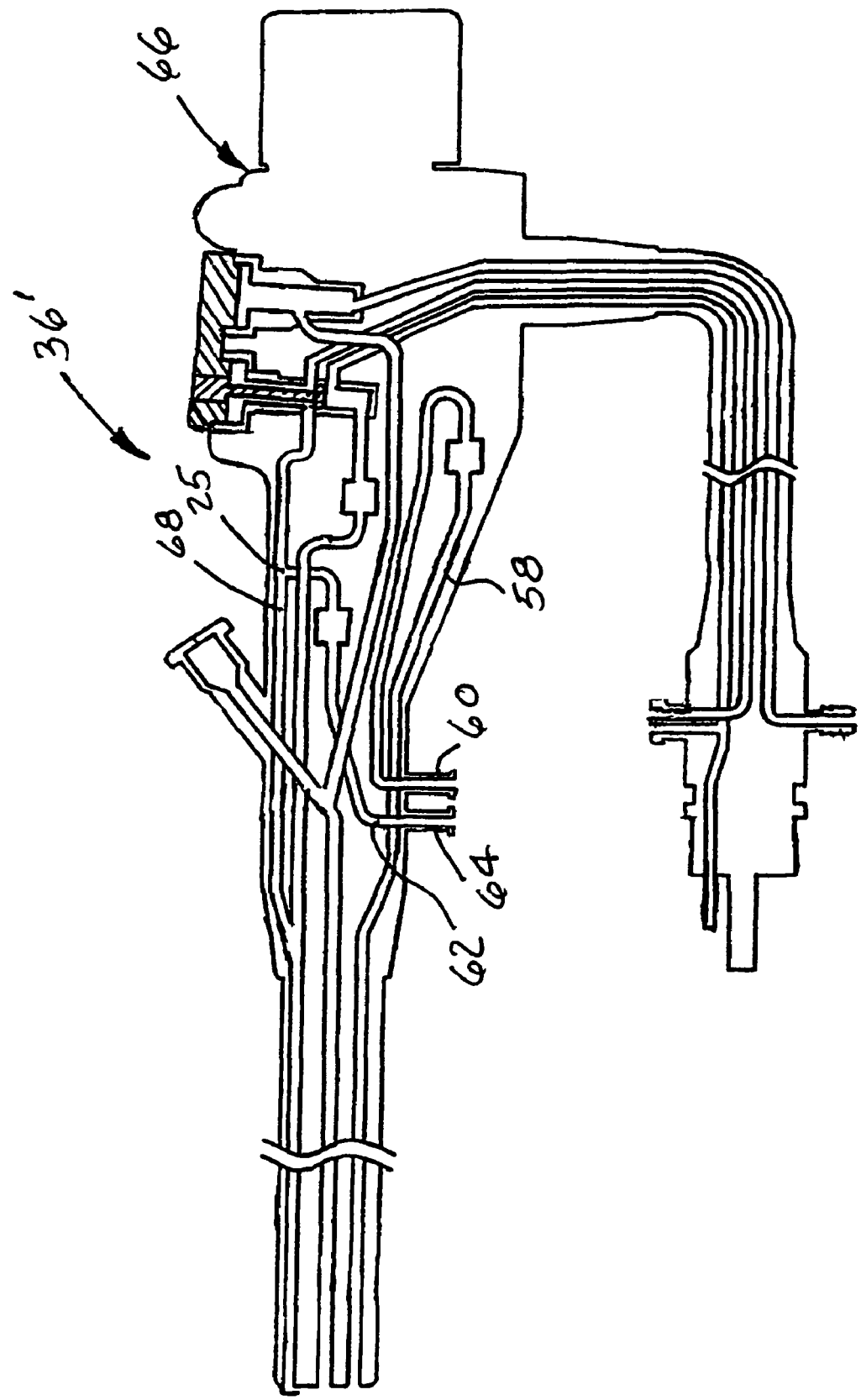
FIG. 4 is a simplified diagrammatic view of another prior art type of endoscope suitable for reprocessing in the practice of the present invention.

Referring now to FIGS. 3 and 4, examples of different types of endoscopes 36, 36' to be reprocessed by the device 30 may be seen. Endoscope 36 is a first type of endoscope and endoscope 36' is a second type of endoscope differing from the first type of endoscope 36 in that it is provided with an additional channel 58 with connection 60 and an additional channel 62 with connection 64. In a head part 66, the channel 62 is connected to an air channel 68 at a joining part 25.

Figure 5:
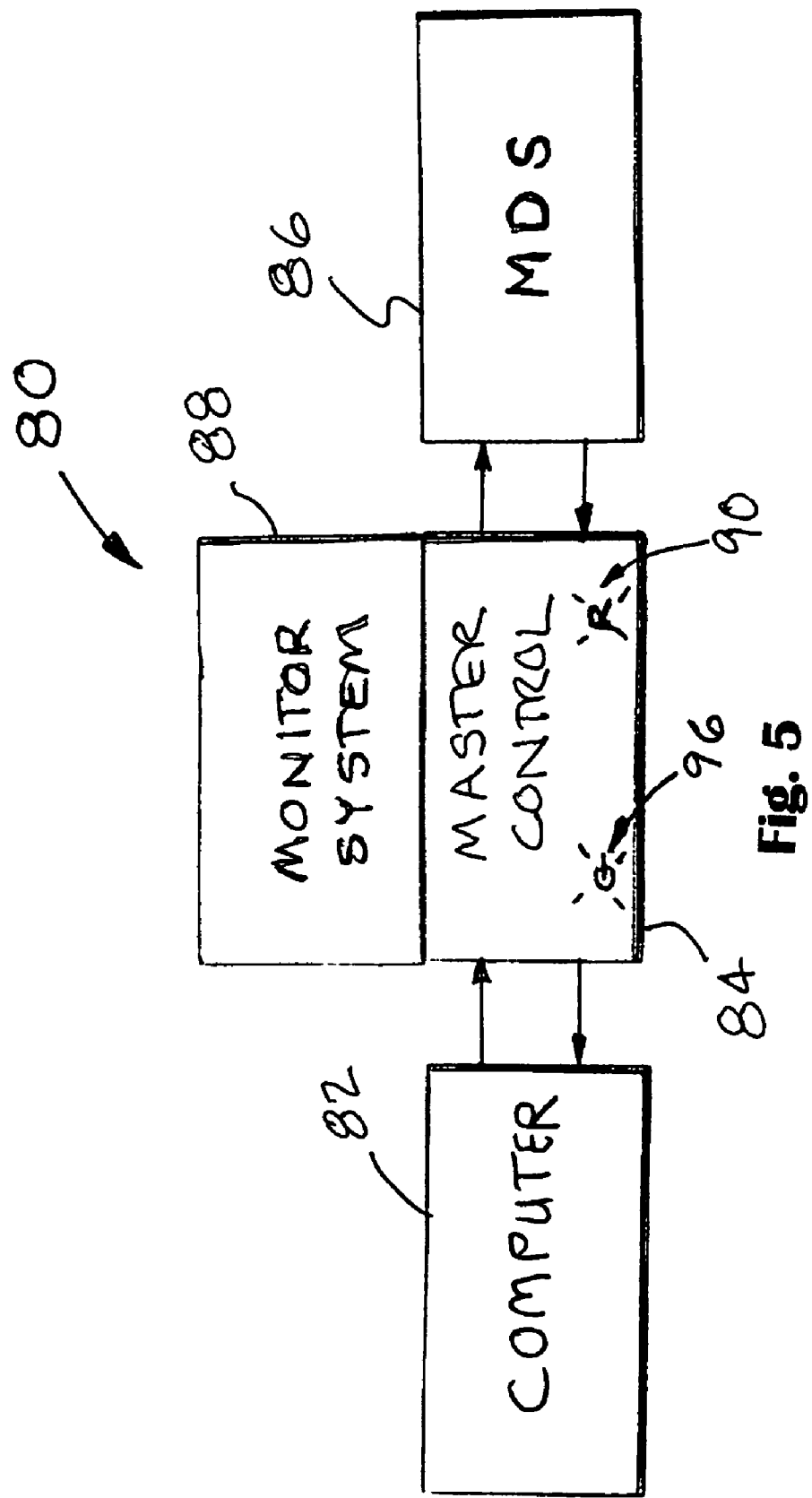
FIG. 5 is a block diagram of the present invention.

Referring now to FIG. 5, a simplified block diagram of the overall system 80 for control of endoscope reprocessing according to the present invention may be seen. Block 82 is a computer (which may be personal computer) programmed to instruct a dedicated endoscope reprocessor (hardware) control in block 86 by way of a master control in block 84. Block 82 is identified as a "COMPUTER." Block 84 may be a programmable logic control identified as an "AS-i master" available from IFM Efector, Inc. at 805 Springdale Drive, Exton, Pa. 19341. Block 86 is identified as an MDS or modular disinfection system, available from Minntech Corporation, 14605 28th Avenue North, Minneapolis, Minn. 55447-4822, and formerly from Dyped Medical BV, Jolweg 22, 1435 KR RIJSENHOUT, Netherlands.

Block 88 is a monitor system that observes the commands from the computer 82 through the master control 84. Blocks 84 and 88 together make up a monitor and control system. Monitor system 88 preferably has an embedded computer software program that mimics and monitors each of the critical steps performed by the applications program in the computer 82 as it instructs and receives data from the MDS 86 through the master control 84. The monitor system 88 takes control of the MDS 86 in the event that an error condition occurs, either in the commands sent by the computer 82 or in the data received from the MDS, or in the event communication is lost with the computer 82. The monitor system 88 prevents the reprocessor 30 from allowing access to an improperly or incompletely processed endoscope 36 contained in basin 31 or 32. This is accomplished by providing a human perceptible signal to the operator of the reprocessor 30, preferably by a visual alarm, such as illuminating a red LED 90 to alert the operator to the less than successful reprocessing of the endoscope then undergoing disinfection and cleaning. The system 80 will continue operation to reach a condition allowing-opening a lid 92 (see FIG. 1) to allow removal of the endoscope then identified as not completely and successfully reprocessed. While lid 92 is shown controlling access to basin 32, it is to be understood that a similar lid controls access to basin 31. Furthermore, it is within the scope of the present invention to utilize means other than a lid to control access to the medical device being processed.

Figure 6:
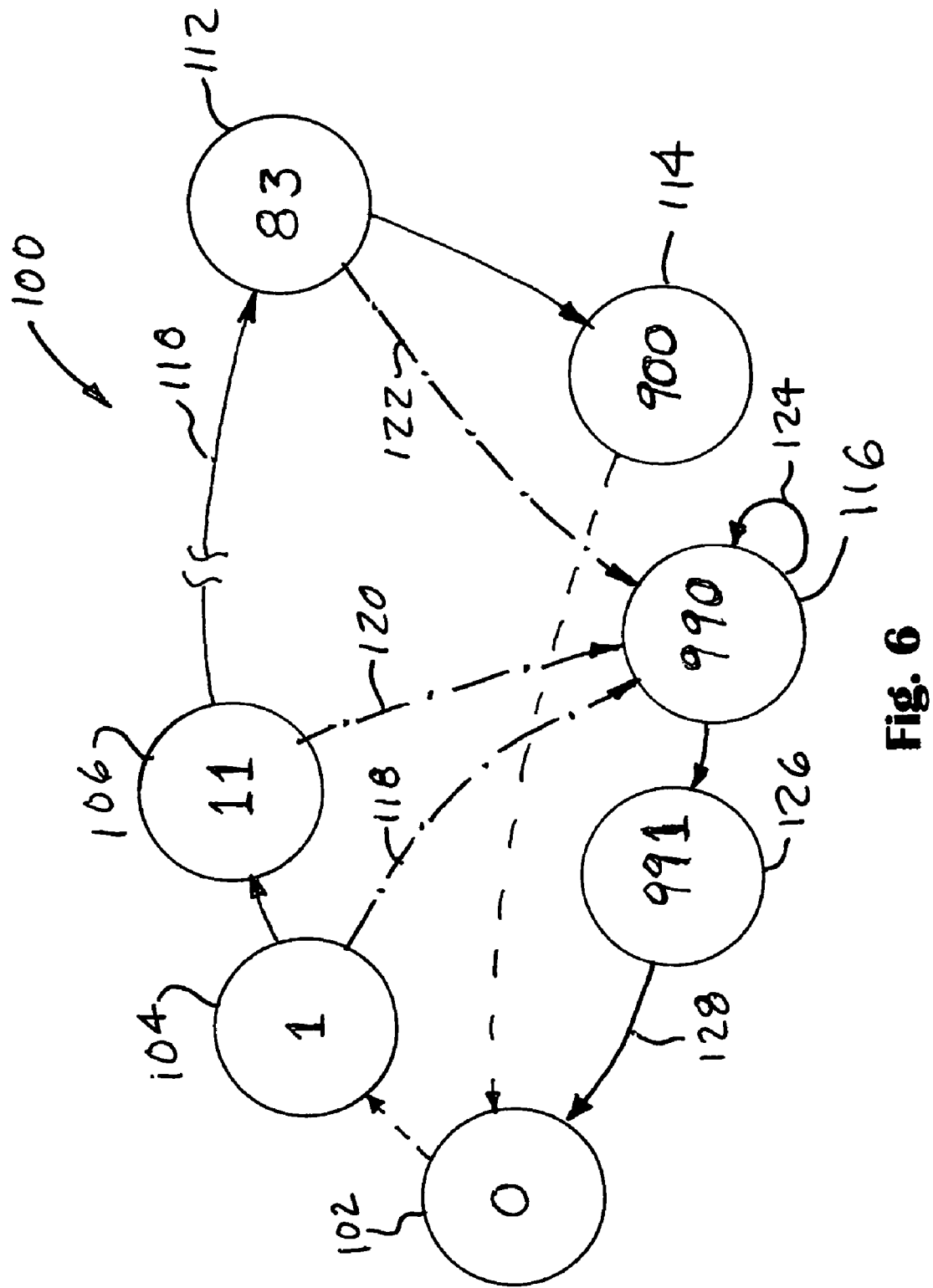
FIG. 6 is a simplified state diagram for the present invention.

Referring now to FIG. 6, a simplified state diagram 100 is shown for the critical steps of the MDS 86 controlled by the computer 82 through the master control 84 and monitored by the monitor system 88. The system will start in a STANDBY state 102, corresponding to step "0" described in more detail infra. When an endoscope 36 is placed in a basin (for example basin 32) and a START button (not shown, but located on device 30) is pushed by the operator, the system goes to a START LEAKTEST state 104, corresponding to critical step 1. If step 1 is performed satisfactorily, the system moves to a PRE-RINSE state 106, corresponding to critical step 11. It is to be understood that software in computer 82 will progress through the states and critical steps (and may also progress through non-critical steps, not shown) unless an error condition is detected. As the system is progressing through the states and critical steps, a parallel program in the monitor system 88 acts like a watchdog, to monitor that the critical steps are successfully and satisfactorily performed under the supervision of the computer-based program. If no error occurs, the system will progress through the critical steps as monitored by the monitor system 88, as indicated by path 110, until the last critical step 83 is reached, corresponding to an AIR RELEASE state 112. Once state 112 and step 83 are successfully completed, the system will progress to state 114 corresponding to a "CORRECT" condition 900, indicating a successful, complete reprocessing sequence has occurred for the endoscope 36 in basin 32. Lid 92 will be released to opened by the operator (for example, by depressing a foot switch, not shown) and a human perceptible indication given, such as causing a flashing illumination of a green LED 96 (see FIG. 5). The green LED 96 may be held continuously ON during successful progress through the states 1 through 83 to indicate that reprocessing is progressing normally.

In the event an error condition occurs in any of the critical steps, the monitor system 88 will override any commands from the computer 82 and drive the system to an error state 116 corresponding to an ERROR condition 990, as indicated by paths 118, 120 and 122. It is to be understood that state 116 can be reached from any critical step state, whether shown in FIG. 6 or not. The critical steps for system 80 are listed in FIG. 10, and are described more fully infra.

Once an error condition occurs, the monitor system 88 will await acknowledgement of the error condition by the computer 82, indicated by the path 124. At this time, the monitor system prevents opening the lid or otherwise providing access to the medical device such as the endoscope undergoing reprocessing. Once acknowledgment is received, the system passes to an ERROR (Lid open) condition 991, indicated by state 126. At this time, the computer 82 proceeds to clear itself to an idle condition preferably after logging the error condition, and the system returns along path 128 to the STANDBY state 102.

In the event that communication is lost between master control 84 and the computer 82, the monitor system 88 will take control of the MDS 86 until communication with computer 82 is re-established.

Figure 7:
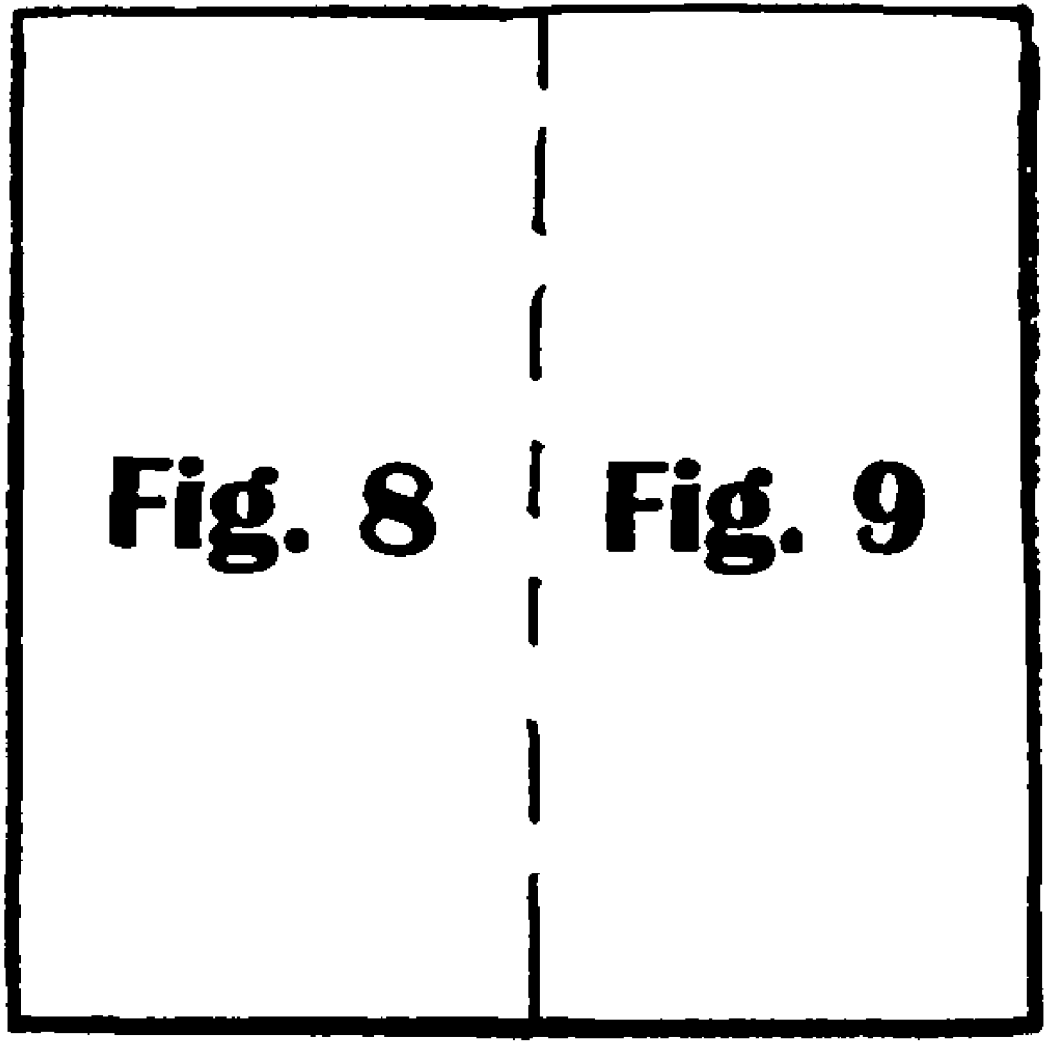
FIG. 7 is a key for FIGS. 8 and 9.
Figure 8:
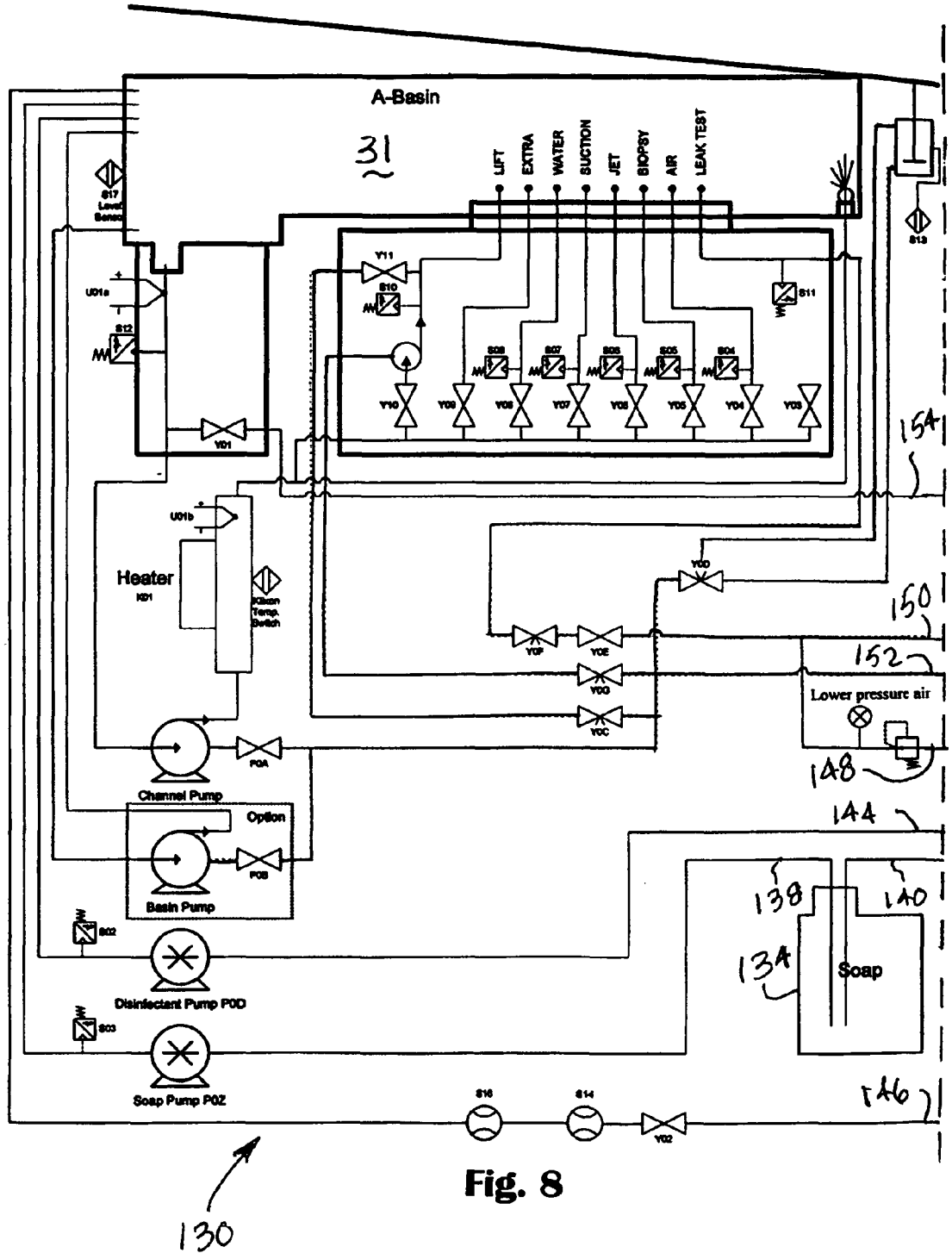
FIG. 8 is a first portion of an example hydraulic schematic for a reprocessor useful in the practice of the present invention.
Figure 9:
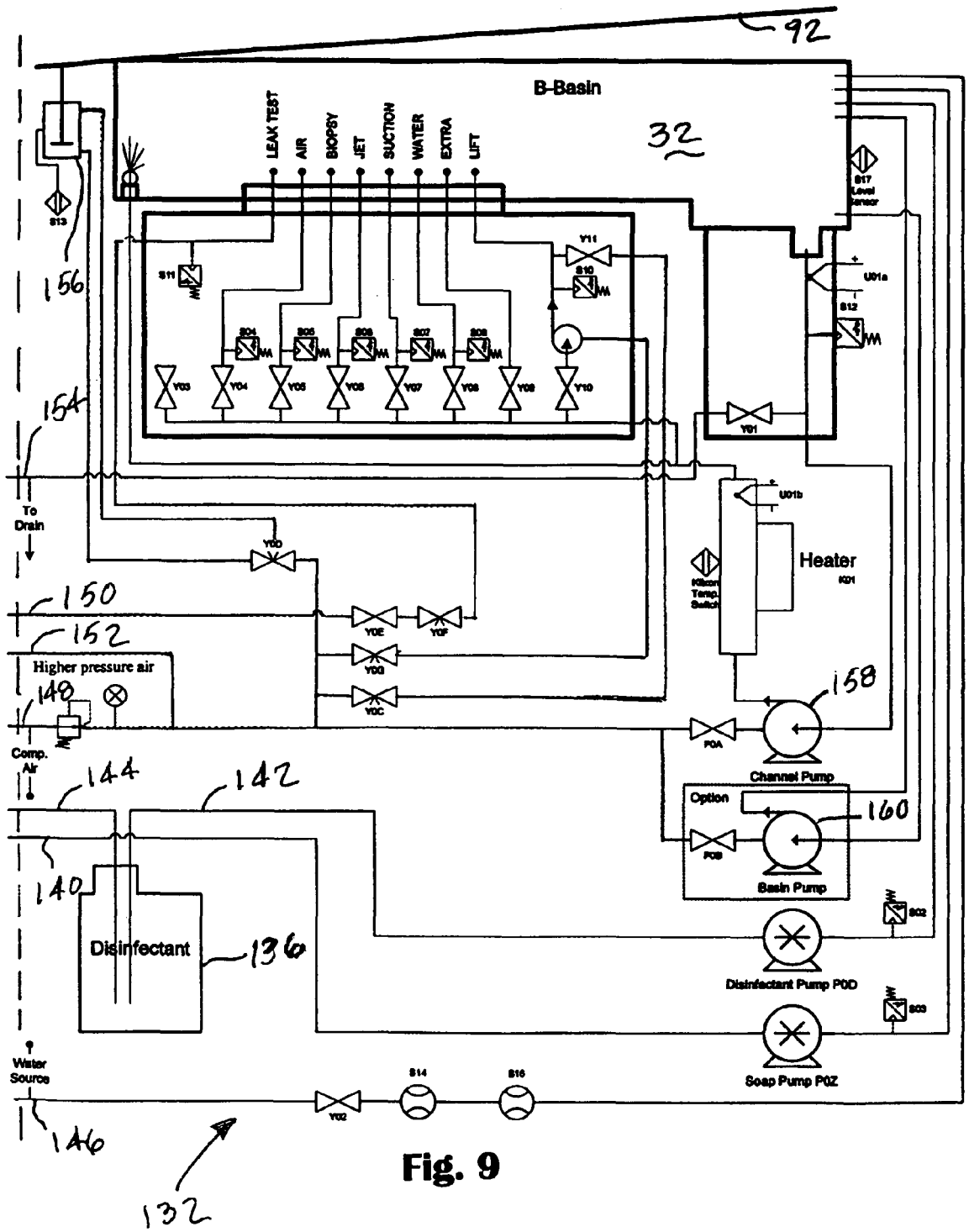
FIG. 9 is a second portion of the schematic of FIG. 8.

Referring now to FIGS. 7, 8 and 9, a hydraulic schematic for the practice of the present invention may be seen. FIG. 7 is a key to illustrate the arrangement of FIGS. 8 and 9. FIG. 8 is a schematic or circuit 130 for the A basin 31, and FIG. 9 is a schematic or circuit 132 for the B basin 32. Lid 92 is shown schematically in FIG. 9. It is to be understood that both a soap reservoir 134 and a disinfectant reservoir 136 are shared by each circuit 130 and 132. Circuit 130 uses a first soap supply line 138, while circuit 132 uses a second soap supply line 140. Circuit 132 uses a first disinfectant supply line 142, while circuit 130 uses a second disinfectant supply line 144. It may be also be seen that circuits 130 and 132 are joined at and share the following connections: a water source line 146, a compressed air source line 148, a lower pressure air line 150, preferably supplying air at 0.25 bar, for example, and a higher pressure air line 152 preferably supplying air at 2.0 to 2.4 bar, for example. Circuits 130 and 132 may also share a common drain connection line 154. It is to be understood that the apparatus shown in FIGS. 8 and 9 is preferably contained within the enclosure of device 30 shown in FIG. 1.

Figure 10:
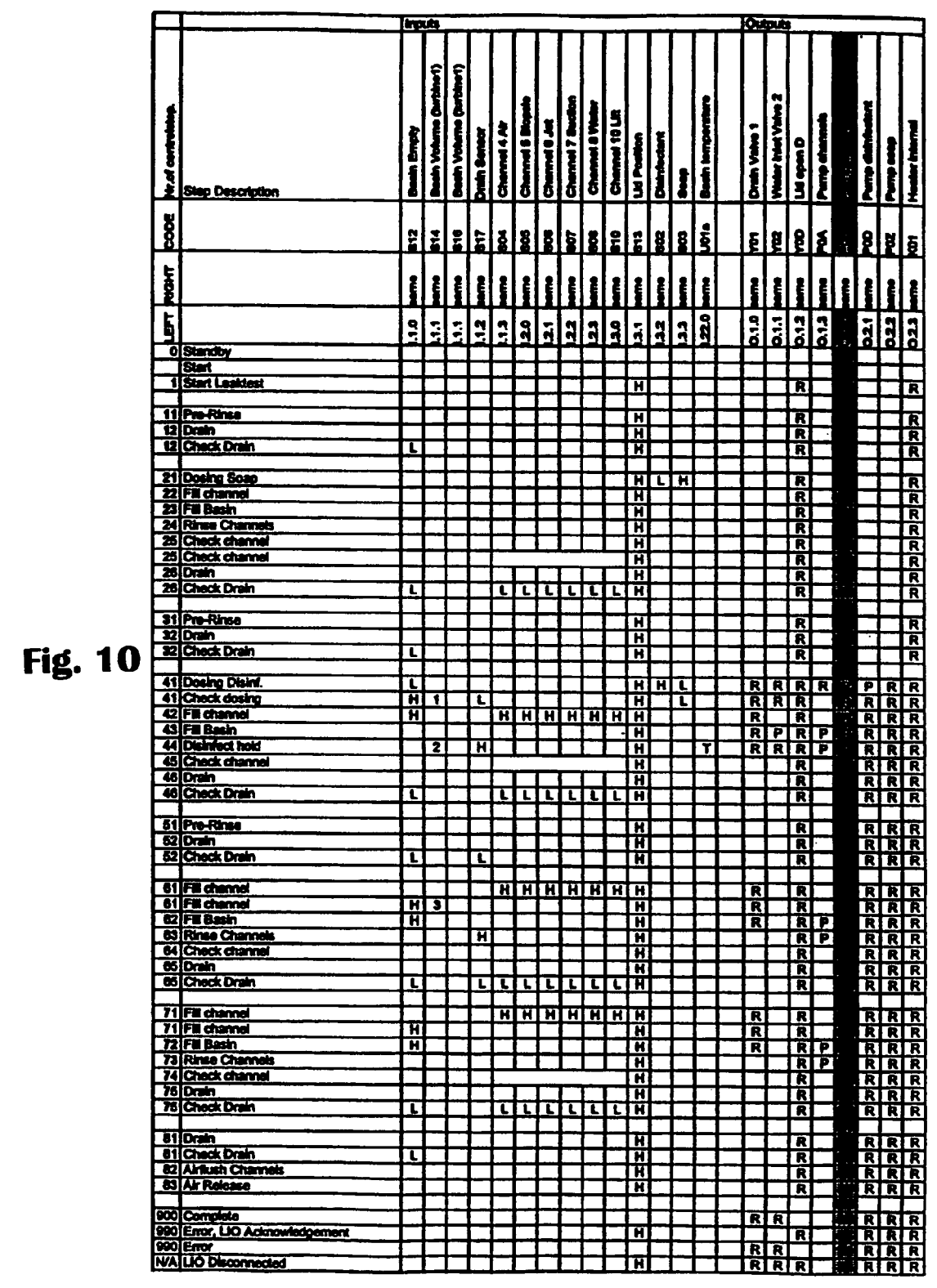

Referring now also to FIGS. 10 and 11, FIG. 10 is a table of critical steps with the number of the step in the left hand column, followed by a step description in the next column, followed by fourteen INPUT columns and eight OUTPUT columns. INPUTS and OUTPUTS are with respect to the computer 82, (and the monitor system 88). The code for each of the INPUTS and OUTPUTS in the table of FIG. 10 identifies the specific corresponding element in the circuits 130 and 132. It is to be understood that each of circuits 130 and 132 may operate independently of the other circuit to independently reprocess separate endoscopes 36 in the respective basins 31 and 32. The operations with respect to basins 31 and 32 are asynchronous with respect to each other, and may or may not be the same, depending upon the type of endoscope being reprocessed at the time. It is to be understood that the type of endoscope may be manually input to the system 80, or may be automatically read, by means of an RF (radio frequency readable) tag or bar code tag associated with the endoscope to be reprocessed.

Inputs

Referring now to FIGS. 10, 8 and 9, the inputs to the computer 82 and monitor system 88 are as follows. Two basin volume turbine sensors S14 and S16 are connected in series to provide redundant backup signals in the event of a single turbine failure. Level sensor S12 provides an indication of whether or not the basin is empty. Drain sensor S17 provides an indication of the level of liquid in the basin. The Channel sensors S04, S05, S06, S07, S08 and S10 provide indications of the status of the respective channels in the endoscope to which they are attached and in fluid communication. Lid position sensor S13 provides an indication of whether or not the respective lid of the respective basin (such as lid 92 for basin 32) is open. Disinfectant sensor S02 provides an indication that disinfectant is being supplied by the disinfectant pump P0D. Similarly, soap sensor S03 provides an indication that soap is being supplied by the soap pump P0Z. A basin temperature sensor U01a provides an indication of the temperature of the liquid in the respective basin, and is used by the system 80 to determine whether the temperature of the liquid is within predetermined limits.

Outputs

Still referring to FIGS. 10, 8 and 9, the outputs to the computer 82 and monitor system 88 are as follows. A drain valve 1, identified by Code Y01, may be commanded to selectively open and close drain line 154 to the respective basin. Water inlet valve 2, identified by Code Y02, may be commanded to selectively supply water from water source line 146 to the respective basin. Lid open D valve Y0D may be commanded to selectively open the lid of the respective basin, for example lid 92 for basin 32 may be opened by valve Y0D acting through a pneumatic cylinder 156. (The position of the lid is concurrently sensed by sensor S13 and provided to system 80). Pump channels valve P0A may be selectively commanded to open or close a connection between channel pump 158 and the higher pressure air line 152 to selectively activate pump 158. Pump sprayer valve P0B may be selectively commanded to open or close a connection between basin pump 160 and the higher pressure air line 152 to selectively activate pump 160. Disinfectant pump P0D may be selectively activated to supply disinfectant from reservoir 136 via line 142 or 144 to basins 32 or 31, respectively. Soap pump P0Z may be selectively activated to supply soap from reservoir 134 via line 138 or 140, respectively, for basins 31 or 32. Heater (internal) K01 may be selectively activated to heat liquid delivered to the respective basin by the channel pump 158.

Although in some instances reference has been made to certain operating elements in one of FIG. 8 or 9, it is to be understood that the same description applies to corresponding elements in the other of FIG. 8 or 9.

Key for FIG. 10

FIG. 11 is a table of abbreviations used in the table of FIG. 10.

Critical Steps

The following is an itemization of one example of a series of critical steps of the MDS 86 carried out by instructions from the computer 82 and monitored by the monitor system 88. Instructions from computer 82 are received as OUTPUTS by master control 84 and acted upon by commands sent to the MDS 86 with consequent action taken in device 30. Signals as INPUTS from the sensors are transmitted from the MDS 86 to the master control 84 and computer 82, with both OUTPUTS and INPUTS monitored by monitor system 88.

The following general checks are performed in steps 1 through 83:
   H02=LED red=Released (100%)
   H01=LED green=Powered (100%)
The following general checks are performed in steps 1 though 991:
   S13=lid position=High (100%)
   K01=heater=Released (100%)
   X01=heart beat=connected, flashing
   =Flow calibration #01=within limits
   =Flow calibration #02=within limits
   S14/S16=Flow Sensors=Checked to within a specified tolerance after a predetermined volume delay
The following are checks performed in all steps except 0, 900 and 991:
   Y0D=lid valve=Driven Released (100%)
Example critical steps performed by the MDS are as follows:

1. Start Leaktest (FL-SL)

The step time is between a minimum of zero and a selected predetermined maximum time. The endoscope is tested in this step to determine if there are any leaks in the channels of the endoscope. Lower pressure air is introduced to the interior of the endoscope, i.e., to the space between the casing and the channels. If a leak is found, the endoscope is not suitable for reprocessing and an indication thereof is given by the system 80 to the operator to remove the endoscope from the reprocessing queue.

11. Pre Rinse (FS-ST)

The step time is between a minimum of zero and a selected predetermined maximum time. The endoscope is rinsed with water in this step to flush debris from the endoscope.

12. Drain (FS-SD)

The step time is between a minimum of zero and a selected predetermined maximum time.
   S12=basin empty=low, at end
   The basin is drained in this step.

21. Dosing Soap (FV-SD)

The step time is between a selected predetermined minimum time and a selected predetermined maximum time.
   S02=disinfectant sensor=low (100%)
   S03=soap sensor=high
      Minimum preselected Time
      Maximum preselected Time 22. Fill Channels (FV-SK)

The step time is between a selected predetermined minimum time and a selected predetermined maximum time.

23. Fill Basin (FV-SV)

The step time is between a minimum of zero and a selected predetermined maximum time.

24. Rinse Channels (FV-SS)

The step time is between a minimum time equal to a selected predetermined time less the Step 23 time and a selected predetermined maximum time.

25. Check Channels (FV-SC)

The step time is between a minimum of zero and a selected predetermined maximum time.

26. Drain (FV-SR)

The step time is between a selected predetermined minimum time and a selected predetermined maximum time.
   S12=basin empty=low, at end
   S04=channel 4 air=low, at end
   S05=channel 5 biopsy=low, at end
   S06=channel 6 jet=low, at end
   S07=channel 7 suction=low, at end
   S08=channel 8 water=low, at end
   S10=channel 10 lift=low, at end
   In steps 21 through 26, soap and water are supplied to the endoscope and basin, filling the endoscope channels and supplying the basin with the solution, after which the channels are rinsed and the endoscope and basin are drained.

31. Pre Rinse (FS-ST)

The step time is between a minimum of zero and a selected predetermined maximum time.

32. Drain (FS-SR)

The step time is between a minimum of zero and a selected predetermined maximum time.
   S12=basin empty=low, at end
   Pre rinsing is repeated in step 31 and the basin emptied in step 32.

41. Dosing disinfectant (FD-SD) Until Pressure Switch is Satisfied
   The step time is between a selected predetermined minimum time and a selected predetermined maximum time.
   S03=soap sensor=Low (100%)
   S02=disinfectant sensor=high
      Minimum predetermined time
      Maximum predetermined time
   Y01=drain valve=Released (100%)
   Y02=water inlet valve=Released (100%)
   P0A=pump channel=Released (100%)
   P0D=pump disinfectant=Powered
      Minimum predetermined time
      Maximum predetermined time
   P0Z=pump soap=Released (100%)
   S12=basin empty=low, at beginning
      =high, at end
   S14=basin volume (turbine)≦Predetermined volume
   S17=drain sensor=Low, at end 42. Fill Channels (FD-SK)
   The step time is between a selected predetermined minimum time and a selected predetermined maximum time.
   Y01=drain valve=Released (100%)
   P0D=pump disinfectant=Released (100%)
   P0Z=pump soap=Released (100%)
   S04=channel 4 air=high, for a predetermined time
   S05=channel 5 biopsy=high, for a predetermined time
   S06=channel 6 jet=high, for a predetermined time
   S07=channel 7 suction=high, for a predetermined time
   S08=channel 8 water=high, for a predetermined time
   S10=channel 10 lift=high, for a predetermined time
   S12=basin empty=high (100%)

43. Fill Basin (FD-SV)
   The step time is between a minimum of zero and a selected predetermined maximum time.
   Y01=drain valve=Released (100%)
   Y02=water inlet valve=Powered (100%)
   P0D=pump disinfectant=Released (100%)
   P0Z=pump soap=Released (100%)
   P0A=pump channel=Powered (100%)

44. Disinfectant Hold (FD-SS)
   The step time is between a minimum time equal to a selected predetermined time less the Step 43 time and a selected predetermined maximum time.
   U01a=temperature basin=minimum predetermined temperature =maximum predetermined temperature
   S14=basin volume (turbine)<predetermined volume
   Y01=drain valve=Released (100%)
   Y02=water inlet valve=Released (100%)
   P0D=pump disinfectant=Released (100%)
   P0Z=pump soap=Released (100%)
   S17=drain sensor=High (100%)
   P0A=pump channel=Powered (100%)

45. Check Channel (FD-SC)
   The step time is between a minimum of zero and a selected predetermined maximum time.
   P0D=pump disinfectant=Released (100%)
   P0Z=pump soap=Released (100%)

46. Drain (FD-SR)
   The step time is between a selected predetermined minimum time and a selected predetermined maximum time.
   S12=basin empty=low, at end
   P0D=pump disinfectant=Released (100%)
   P0Z=pump soap=Released (100%)
   S04=channel 4 air=low, at end
   S05=channel 5 biopsy=low, at end
   S06=channel 6 jet=low, at end
   S07=channel 7 suction=low, at end
   S08=channel 8 water=low, at end
   S10=channel 10 lift=low, at end In steps 41 through 46, the endoscope and basin are supplied with a solution of disinfectant and water which fills and recirculates through the channels of the endoscope and a flow through check or test is performed on the channels, after which the endoscope and basin is drained.

51. Pre Rinse (FS-ST)
   The step time is between a minimum of zero and a selected predetermined maximum time.
   P0D=pump disinfectant=Released (100%)
   P0Z=pump soap=Released (100%)

52. Drain (FS-SD)
   The step time is between a minimum of zero and a selected predetermined maximum time.
   S12=basin empty=low, at end
   P0D=pump disinfectant=Released (100%)
   P0Z=pump soap=Released (100%)
   S17=drain sensor=Low, at end A further pre rinse and drain with water is performed in steps 51 and 52.

61. Fill Channels (FS-SK)
   The step time is between a selected predetermined minimum time and a selected predetermined maximum time.
   S12=basin empty=high, at end
   Y01=drain valve=Released (100%)
   S04=channel 4 air=high, for predetermined time
   S05=channel 5 biopsy=high, for predetermined time
   S06=channel 6 jet=high, for predetermined time
   S07=channel 7 suction=high, for predetermined time
   S08=channel 8 water=high, for predetermined time
   510=channel 10 lift=high, for predetermined time
   P0D=pump disinfectant=Released (100%)
   P0Z=pump soap=Released (100%)

62. Fill Basin (FN-SV)
   The step time is between a selected predetermined minimum time and a selected predetermined maximum time.
   S12=basin empty=high (100%)
   Y01=drain valve=Released (100%)
   P0D=pump disinfectant=Released (100%)
   P0Z=pump soap=Released (100%)
   P0A=pump channel=Powered (100%)

63. Rinse Channels (FN-SS)
   The step time is between a minimum time equal to a selected predetermined time less the Step 62 time and a selected predetermined maximum time.
   P0D=pump disinfectant=Released (100%)
   P0Z=pump soap=Released (100%)
   S17=drain sensor=High (100%)
   P0A=pump channel=Powered (100%)

64. Check Channels (FN-SC)
   The step time is between a minimum of zero and a selected predetermined maximum time.
   P0D=pump disinfectant=Released (100%)
   P0Z=pump soap=Released (100%)

65. Drain (FS-SR)
   The step time is between a selected predetermined minimum time and a selected predetermined maximum time.
   S12=basin empty=low, at end S04=channel 4 air=low, at end
S05=channel 5 biopsy=low, at end
S06=channel 6 jet=low, at end
S07=channel 7 suction=low, at end
S08=channel 8 water=low, at end
S10=channel 10 lift=low, at end
P0D=pump disinfectant=Released (100%)
P0Z=pump soap=Released (100%)
S17=Drain Sensor=Low, at end In steps 61 through 65 the channels of the endoscope and the basin are supplied with water and rinsed, checked and drained.

71. Fill Channels (FN-SK)

The step time is between a selected predetermined minimum time and a selected predetermined maximum time.
Y01=drain valve=Released (100%)
S04=channel 4 air=high, once for a predetermined time
S05=channel 5 biopsy=high, once for a predetermined time
S06=channel 6 jet=high, once for a predetermined time
S07=channel 7 suction=high, once for a predetermined time
S08=channel 8 water=high, once for a predetermined time
S10=channel 10 lift=high, once for a predetermined time
S12=basin empty=high, at end
P0D=pump disinfectant=Released (100%)
P0Z=pump soap=Released (100%)

72. Fill Basin (FN-SV)

The step time is between a minimum of zero and a selected predetermined maximum time.
S12=basin empty=high (100%)
Y01=drain valve=Released (100%)
P0D=pump disinfectant=Released (100%)
P0Z=pump soap=Released (100%)
P0A=pump channel=Powered (100%)

73. Rinse Channels (FN-SS)

The step time is between a minimum time equal to a selected predetermined time less the Step 72 time and a selected predetermined maximum time.
P0D=pump disinfectant=Released (100%)
P0Z=pump soap=Released (100%)
P0A=pump channel=Powered (100%)

74. Check Channels (FN-SC)

The step time is between a minimum of zero and a selected predetermined maximum time.
P0D=pump disinfectant=Released (100%)
P0Z=pump soap=Released (100%)

75. Drain (FN-SR)

The step time is between a selected predetermined minimum time and a selected predetermined maximum time.
S12=basin empty=low, at end
P0D=pump disinfectant=Released (100%)
P0Z=pump soap=Released (100%)
S04=channel 4 air=low, at end
S05=channel 5 biopsy=low, at end
S06=channel 6 jet=low, at end
S07=channel 7 suction=low, at end
S08=channel 8 water=low, at end
S10 channel 10 lift=low, at end In steps 71 through 75 the channels of the endoscope and the basin are again supplied with water and rinsed, checked and drained.

81. Drain (FA-SB)

The step time is between a minimum of zero and a selected predetermined maximum time.
S12=basin empty=low, at end
P0D=pump disinfectant=Released (100%)
P0Z=pump soap=Released (100%)

82. Airflush Channels (FA-SR)

The step time is between a selected predetermined minimum time and a selected predetermined maximum time.
P0D=pump disinfectant=Released (100%)
P0Z=pump soap=Released (100%)

83. Air Release (FA-SO)

The step time is between a minimum of zero and a selected predetermined maximum time.
P0D=pump disinfectant=Released (100%)
P0Z=pump soap=Released (100%)

In steps 81 through 83, the basin is kept in an open drain condition, and the endoscope is flushed with air.

900. Correct, (Lid open)

Step time=until cover open
Y01=Drain Valve=Driven Powered (100%)
Y02=water inlet valve 2=Driven Released (100%)
K01=heater=Driven Released (100%)
P0D=pump disinfectant=Driven Released (100%)
P0Z=pump soap=Driven Released (100%)
H02=LED red=Released (100%)
H01=LED green=powered, flashing Once the reprocessing is successfully completed, the lid is opened and the green LED is switched from a continuous illumination to a flashing mode, indicating reprocessing is complete.

990. Error LIO Acknowledgement

Step time=until error acknowledged from LIO (LIO refers to the computer 82
P0D=pump disinfectant=Driven Released (100%)
P0Z=pump soap=Driven Released (100%)
H01=LED green=Released (100%)
H02=LED red=powered, 100%

The red LED is continuously illuminated to indicate an error condition.

991. Error, (Lid Open)

Step time=until lid open
Y01=Drain Valve=Driven Powered (100%)
Y02=water inlet valve 2=Driven Released (100%)
K01=heater=Driven Released (100%)
P0D=pump disinfectant=Driven Released (100%)
P0Z=pump soap=Driven Released (100%)
H01=LED green=Released (100%)
H02=LED red=powered, 100%

When an error condition exists, after acknowledgement by the computer (and operator, if desired) the lid is opened to allow removal of the incompletely reprocessed endoscope. The red LED is illuminated.

0 Standby

Step time=unlimited
H01=LED green=Released after Power On
H02=LED Red=Released after Power On
X01=heart beat=connected, flashing In the standby state, both the red and green LEDs are not illuminated, and the system is waiting to commence reprocessing.

LIO disconnected (refers to loss of communication with computer 82)
Step time=until connected
Y0D=lid valve=Driven Released (100%)
Y01=Drain Valve=Driven Powered (100%)
Y02=water inlet valve 2=Driven Released (100%)
K01=heater=Driven Released (100%)
P0D=pump disinfectant=Driven Released (100%)
P0Z=pump soap=Driven Released (100%)
H01=LED green=Released (100%)
H02=LED red=powered (100%)
X01=heart beat=connected, flashing The heart beat refers to a form of hand-shake signal between the computer 82 and the master control 84 repeatedly made to confirm that two-way communication between the computer 82 and the master control 84 is present. The red LED is illuminated for this condition.

Although not described above, it is within the operation of the system 80 and device 30 to perform self-disinfecting, according to a set of critical steps similar to those for endoscope reprocessing, if desired, and such a self-disinfecting process may be monitored by the monitor system 88 and be within the scope of the present invention.

It may thus be seen that the present invention is a method and apparatus for monitoring critical steps of a process, more particularly, a medical device process, and even more particularly, an endoscope reprocessing process wherein the endoscope is cleaned and disinfected. Alternatively, the process of sterilization may replace disinfection. Furthermore, the present invention may be used with a process that includes only one, or two or three of these activities of cleaning and disinfecting and sterilizing. During the process, a monitor system checks both inputs and outputs with respect to a computer which may have a conventional operating system. The monitor system 88 has a custom embedded version of software to monitor the critical steps to be sure they are performed and performed correctly. The monitor system 88 allows for changes in the operating systems and applications programs in the computer 82 (and or in any networks connected to the computer 82) while not requiring a failure mode and criticality analysis to be performed on the operating system of computer 82 or applications programs of the computer 82. The embedded software in the monitor system 88 checks the operation of the overall system 80 normally under control of the computer 82 and overrides or takes control when an error occurs in a critical step of the operation. The critical steps are determined in advance of operation. In an alternative embodiment, the monitor system 88 and master control 84 may be combined together.

In one aspect, the present invention is an apparatus for monitoring critical steps in the reprocessing of endoscopes in a system of the type having a computer (which may be a personal computer or any other type of reprogrammable computer) controlling a reprocessing device through a master control, which may be a programmable logic controller. The apparatus for monitoring critical steps includes a monitor system having an embedded monitoring program which tracks the critical steps in the reprocessing. The embedded monitoring program may be a "mirror" or image of the program containing the reprocessing critical steps. In the practice of one embodiment of the present invention, the monitor system compares the actual reprocessing step to the corresponding step in the monitor image program, and verifies whether the step is correct or not. If it is correct, the reprocessing is allowed to continue. If an error in a critical step is observed, the monitor system will take control of the reprocessing and signal the personal computer that an error has occurred. A perceptible indication is also preferably given to the operator of the reprocessing device, to signal the operator that the endoscope has not been properly reprocessed. Access to the endoscope during normal reprocessing and during an error condition is controlled by a means for providing selectively operable access such as a lid on a basin containing the endoscope in question. Once successful reprocessing has occurred, or the error reported appropriately, the lid is allowed to be opened (or the alternative means for providing access are selectively operated or enabled) to allow access to the endoscope (or other medical device being processed).

The present invention is particularly applicable to reprocessing medical and other devices that are thermolabile, i.e., that would be subject to breakdown or degradation if heat were to be applied to raise the temperature sufficient to sterilize such devices.

In one aspect of the present invention a predetermined set of critical steps (e.g., steps corresponding to states 104, 106 and 112) must each be completed and completed in a specified predetermined order. In other words in this aspect, the monitor system 88 looks to see that each of the predetermined critical steps is performed, and performed satisfactorily (i.e., within specified parameter limits, if applicable) and performed in a desired sequence. The monitor will only allow the overall system to reach the last step indicating successful completion of the process related to the critical steps (e.g., successfully reprocessing an endoscope, indicated by step 900 in the endoscope reprocessing example process described above) after the system successfully completes all of the previous critical steps and in the correct order. However, it is to be further understood that "non-critical" steps may be performed (with or without specified parameters) or omitted (or possibly performed in a different order) while still remaining within the spirit and scope of the present invention, as long as the critical steps aspect of the present invention is practiced.

In the practice of the present invention as applied to endoscope reprocessing, it is to be understood that only one basin and control system and apparatus may be used, or that more than two basins and control systems may be used. Furthermore, additional or fewer or different critical steps may be used while practicing the present invention, either for endoscope reprocessing or for another "critical steps" process or apparatus.

This invention is not to be taken as limited to all of the details thereof as modifications and variations thereof may be made without departing from the spirit or scope of the invention.

What is claimed is:

1. An apparatus for reprocessing a device, the apparatus comprising:
    a. a computer controlling a device reprocessing system using a reprocessing program, the reprocessing program including a set of critical steps in reprocessing the device, each critical step including one or more program inputs to the computer from the device reprocessing system, the one or more program inputs including sensed operational parameters from the device reprocessing system, each critical step further including one or more program outputs from the computer to the device reprocessing system, the one or more program outputs including control signals to the device reprocessing system to perform reprocessing operations during the reprocessing of the device;
    b. a monitor and control system separate from the computer that monitors inputs to and outputs from the computer during the reprocessing of the device and executes a monitoring program in parallel with the reprocessing program, the monitoring program having a copy of at least the set of critical steps of the reprocessing program;

wherein the monitor and control system is connected to the computer and the device reprocessing system and wherein the monitor and control system tracks the critical steps executed by the computer in the reprocessing program with the monitoring program monitoring performance of the critical steps, and wherein the monitor and control system stops the computer from continuing execution of the reprocessing program with the device reprocessing system when an error associated with a critical step is detected, the monitor and control system detecting the error when at least one of the inputs to the computer or outputs from the computer during the reprocessing of the device does not match the one or more program inputs and one or more program outputs associated with the critical step.

2. The apparatus of claim 1 further comprising an error condition indicator indicating when an error associated with a critical step has been detected.

3. The apparatus of claim 2 wherein the indicator provides a human perceptible indication.

4. The apparatus of claim 1 wherein the device is an endoscope.

5. The apparatus of claim 1 wherein the monitor and control system compares an actual reprocessing step from the reprocessing program to a corresponding copy of the step in the monitoring program, and verifies whether the actual step in the reprocessing program is correct or not.

6. The apparatus of claim 1 wherein the monitor and control system includes a programmable logic controller.

7. A control assembly for a device reprocessing system for reprocessing a medical device, the control assembly comprising:

a first processing device that controls the device reprocessing system based on a reprocessing program executed by the first processing device, wherein the reprocessing program includes a set of critical steps in reprocessing the medical device, each critical step including one or more program inputs to the first processing device from the device reprocessing system, the one or more program inputs including sensed operational parameters from the device reprocessing system, each critical step further including one or more program outputs from the first reprocessing device to the device reprocessing system, the one or more program outputs including control signals to the device reprocessing system to perform reprocessing operations during the reprocessing of the device; and a second processing device connected between the first processing device and the device reprocessing system, wherein the second processing device monitors inputs to and outputs from the first processing device during the reprocessing of the medical device and executes a monitoring program including the set of critical steps in parallel with execution of the reprocessing program to monitor performance of the set of critical steps, wherein the second processing device stops execution of the reprocessing program by the first processing device when the second processing device detects an error in the performance of a critical step, the second processing device detecting the error when at least one of the inputs to the first processing device or outputs from the first processing device during the reprocessing of the medical device does not match the one or more program inputs and one or more program outputs associated with the critical step.

8. The control assembly of claim 7, and further comprising: an error condition indicator indicating when the error in the performance of a critical step is detected.

9. The control assembly of claim 8, wherein the error condition indicator comprises a human perceptible indication.

10. The control assembly of claim 7, wherein the device is an endoscope.

11. The control assembly of claim 7, wherein the second processing device compares a critical step from the reprocessing program to a corresponding critical step in the monitoring program to verify performance of the critical step in the reprocessing program.

12. The control assembly of claim 7, wherein the second processing device includes a programmable logic controller.

13. The control assembly of claim 7, wherein the second processing device further removes control of the device reprocessing system from the first processing device when the second processing device detects an error in the performance of a critical step.

14. The control assembly of claim 13, wherein, when the second processing device detects an error in the performance of a critical step, the second processing device prevents access to the medical device in the device reprocessing system until the second processing device receives acknowledgement from the first processing device that the error has occurred.

15. The control assembly of claim 7, wherein, when communication between the first processing device and the device reprocessing system is lost, the second processing device controls the device reprocessing system until communication between the first processing device and the device reprocessing system is reestablished.

16. The control assembly of claim 7, wherein the second processing device detects an error in the performance of a critical step when the critical step is performed incorrectly or out of order.

17. A control assembly for a device reprocessing system for reprocessing a medical device, the control assembly comprising:

a computer that controls the device reprocessing system based on a reprocessing program executed by the computer, wherein the reprocessing program includes a set of critical steps in reprocessing the medical device, each critical step including one or more program inputs to the computer from the device reprocessing system, the one or more program inputs including sensed operational parameters from the device reprocessing system, each critical step further including one or more program outputs from the computer to the device reprocessing system, the one or more program outputs including control signals to the device reprocessing system to perform reprocessing operations during the reprocessing of the device; and a monitor and control system that monitors inputs to and outputs from the computer during the reprocessing of the medical device and executes a monitoring program including the set of critical steps in parallel with execution of the reprocessing program to monitor performance of the set of critical steps, wherein the monitor and control system stops execution of the reprocessing program by the computer and removes control of the device reprocessing system from the computer when the monitor and control system detects an error in the performance of a critical step, the monitor and control system detecting the error when at least one of the inputs to the computer or outputs from the computer during execution of the critical step during reprocessing of the medical device does not match the one or more program inputs and one or more program outputs associated with the critical step.

18. The control assembly of claim 17, wherein the monitor and control system compares a critical step from the reprocessing program to a corresponding critical step in the monitoring program to verify performance of the critical step in the reprocessing program.

19. The control assembly of claim 17, wherein, when the monitor and control system detects an error in the performance of a critical step, the monitor and control system prevents access to the medical device in the device reprocessing system until the monitor and control system receives acknowledgement from the computer that the error has occurred.

20. The control assembly of claim 17, wherein, when communication between the computer and the device reprocessing system is lost, the monitor and control system controls the device reprocessing system until communication between the computer and the device reprocessing system is reestablished.

21. The control assembly of claim 17, wherein the second processing device detects an error in the performance of a critical step when the critical step is performed incorrectly or out of order.

\* \* \* \* \*